(12) United States Patent
Momose et al.

(10) Patent No.: US 10,627,405 B2
(45) Date of Patent: Apr. 21, 2020

(54) DETECTION DEVICE AND BIOLOGICAL INFORMATION MEASURING DEVICE

(71) Applicant: SEIKO EPSON CORPORATION, Tokyo (JP)

(72) Inventors: Yoshihiko Momose, Shiojiri (JP); Hidekazu Kobayashi, Hara-mura (JP); Koya Shiratori, Matsumoto (JP); Takashi Toya, Chino (JP); Makoto Katase, Azumino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 51 days.

(21) Appl. No.: 16/018,590

(22) Filed: Jun. 26, 2018

(65) Prior Publication Data

US 2019/0011453 A1 Jan. 10, 2019

(30) Foreign Application Priority Data

Jul. 6, 2017 (JP) .................................. 2017-132518

(51) Int. Cl.
*G01N 33/66* (2006.01)
*G01N 21/25* (2006.01)
*G01N 21/359* (2014.01)
*G01N 21/3577* (2014.01)
*G01N 21/47* (2006.01)
*A61B 5/145* (2006.01)
(Continued)

(52) U.S. Cl.
CPC ........... *G01N 33/66* (2013.01); *A61B 5/1455* (2013.01); *A61B 5/14532* (2013.01); *G01N 21/255* (2013.01); *G01N 21/359* (2013.01); *G01N 21/3577* (2013.01); *G01N 21/474* (2013.01); *A61B 5/0075* (2013.01); *G01N 2021/4757* (2013.01); *G01N 2201/129* (2013.01)

(58) Field of Classification Search
CPC .. G01N 33/66; G01N 21/3577; G01N 21/359; G01N 21/255; G01N 21/474; G01N 2201/129; G01N 2021/4757; A61B 5/1455; A61B 5/14532; A61B 5/0075; A61B 5/6824; A61B 5/6802
See application file for complete search history.

(56) References Cited

U.S. PATENT DOCUMENTS 3,906,939 A * 9/1975 Aronson ............ A61B 5/02141
600/493
5,377,000 A * 12/1994 Berends .................... G01J 3/51
356/407
(Continued)

FOREIGN PATENT DOCUMENTS

| EP | 2439518 A1 | 4/2012 |
|---|---|---|
| JP | 2005-334281 A | 12/2005 |

(Continued)

*Primary Examiner* — Mohamed K Amara
(74) *Attorney, Agent, or Firm* — Oliff PLC

(57) ABSTRACT

A detection device includes a light source which emits light, a lens, a light transmissive protecting plate, a length between the light source and the light transmissive protecting plate being larger than a length between the lens and the light transmissive protecting plate, and a light receiving element which receives the light. An angle formed by an optical axis of the lens and the light transmissive protecting plate is smaller than an angle formed by an optical axis of the light source and the transmissive protecting plate.

4 Claims, 3 Drawing Sheets

(51) Int. Cl.
 *A61B 5/1455* (2006.01)
 *A61B 5/00* (2006.01)

(56) References Cited

U.S. PATENT DOCUMENTS

| | | | | |
|---|---|---|---|---|
| 5,801,817 | A * | 9/1998 | Riedel | G01B 11/00 356/4.07 |
| 5,825,555 | A * | 10/1998 | Oono | G01C 15/004 359/668 |
| 6,009,339 | A * | 12/1999 | Bentsen | G01N 21/05 600/322 |
| 6,061,583 | A * | 5/2000 | Ishihara | A61B 5/14535 600/322 |
| 6,263,227 | B1 * | 7/2001 | Boggett | A61B 5/0261 356/39 |
| 6,975,898 | B2 * | 12/2005 | Seibel | A61B 1/00048 600/473 |
| 7,136,704 | B2 * | 11/2006 | Schulman | A61N 1/36557 607/22 |
| 7,862,335 | B2 * | 1/2011 | Berube-Lauziere | A61B 5/0088 433/29 |
| 9,877,681 | B2 * | 1/2018 | Silverman | A61K 31/04 |
| 2002/0048307 | A1 * | 4/2002 | Schmidt | G01J 5/08 374/121 |
| 2004/0159799 | A1 * | 8/2004 | Saccomanno | G01N 15/1459 250/461.1 |
| 2012/0057164 | A1 * | 3/2012 | Tezuka | A61B 5/0068 356/445 |
| 2018/0168456 | A1 * | 6/2018 | Lim | G16H 40/63 |

FOREIGN PATENT DOCUMENTS

| | | |
|---|---|---|
| JP | 2009-168670 A | 7/2009 |
| JP | 2010-281751 A | 12/2010 |

* cited by examiner

DETECTION DEVICE AND BIOLOGICAL INFORMATION MEASURING DEVICE

BACKGROUND

1. Technical Field

The present invention relates to a technique for measuring biological information of a subject.

2. Related Art

There has been proposed a technique for measuring biological information of subject. For example, JP-A-2005-334281 (Patent Literature 1) discloses a configuration for measuring component concentration in an organism in a noninvasive manner. Specifically, in the technique disclosed in Patent Literature 1, near infrared light is irradiated toward an organism surface, reflected light from an organism inside is received, and the component concentration in the organism is measured from a biological signal obtained from a received light component.

SUMMARY

In order to highly accurately measure the component concentration in the organism, it is desirable to uniformly irradiate the near infrared light on the organism surface. An advantage of some aspects of the invention is to reduce a difference in the intensity of light (irradiation unevenness) within a range in which the light is irradiated on an organism.

A detection device according to a first aspect of the invention includes: a light emitting section configured to irradiate light on an organism; a light receiving section configured to generate a detection signal corresponding to a light reception level of the light irradiated from the light emitting section and passed through the organism; and an opposed surface opposed to the organism. The light emitting section includes a light source section configured to emit light and a lens through which the light emitted from the light source section passes. An optical axis of the light source section is inclined with respect to the opposed surface. An angle formed by the opposed surface and an optical axis of the lens is smaller than an angle formed by the opposed surface and the optical axis of the light source section. With the configuration explained above, since the optical axis of the light source section is inclined with respect to the opposed surface, it is easy to obtain diffused reflected light reflected from an organism inside. Since the angle formed by the opposed surface and the optical axis of the lens is smaller than the angle formed by the opposed surface and the optical axis of the light source section, it is possible to reduce a difference the intensity of the light (irradiation unevenness) within a range in which the light is irradiated on the organism.

A detection device according to a second aspect of the invention includes: a plurality of light emitting sections configured to irradiate lights on an organism; a light receiving section configured to generate a detection signal corresponding to a light reception level of the lights irradiated from the plurality of light emitting sections and passed through the organism; an opposed surface opposed to the organism; and a light receiving formed from the opposed surface toward the light receiving section. Each of the plurality of light emitting sections includes a light source section configured to emit light and a lens through which the light emitted from the light source section passes and which is located on a circumference around a center axis of the light receiving path. In each of the plurality of light emitting sections, an optical axis oaf the light source section inclined with respect to the opposed surface. An angle formed by the opposed surface and an optical axis of the lens is smaller than an angle formed by the opposed surface and the optical axis of the light source section. With the configuration explained above, since the optical axis of the light source section inclined with respect to the opposed surface, is easy to obtain diffused reflected light reflected from an organism inside. Since the angle formed by the opposed surface and the optical axis of the lens is smaller than the angle formed by the opposed surface and the optical axis of the light source section, it is possible to reduce a difference in the intensity of the light (irradiation unevenness) within a range in which the light is irradiated on the organism.

In a preferred aspect of the invention, an angle formed by the optical axis of the lens and the optical axis of the light source section is 5 degrees or more and 15 degrees or less. With the configuration in which the angle formed by the optical axis of the lens and the optical axis of the light source section is 5 degrees or more and 15 degrees or less, the effect of reducing a difference in the intensity of the light (irradiation unevenness) within the range in which the light is irradiated on the organism is more conspicuous.

A biological information measuring device according to another aspect of the invention includes: the detection device according to the first or second aspect; and a specifying sect n configured to specify biological information from the detection signal generated by the detection device. In the detection device according to the first or second aspect, it is easy to obtain diffused reflected light reflected from the organism inside, it is possible to irradiate uniform light on a measurement part. Therefore, with the biological information measuring device according to the third aspect, it is possible to highly accurately specify biological information.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
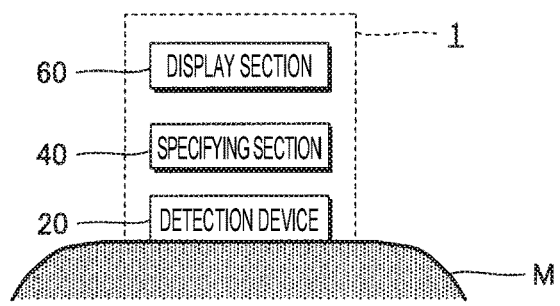
FIG. 1 is a configuration diagram of a biological information measuring device according to an embodiment of the invention.

FIG. 1 is a configuration diagram of a biological information measuring device 1 according to an embodiment of the invention. The biological information measuring device 1 is a measuring device that measures biological information of a subject in a noninvasive manner. In this embodiment, a blood sugar level (glucose concentration) of a user is illustrated as the biological information.

The biological information measuring device according to this embodiment includes a detection device 20, a specifying section 40, and a display section 60. The detection device 20 is an optical sensor module that generates a detection signal corresponding to a state of a part set as a measurement target (hereinafter referred to as "measurement part") M in a body of the user. The biological information measuring device 1 is attached to the surface of the measurement part M (e.g., a wrist).

Figure 2:
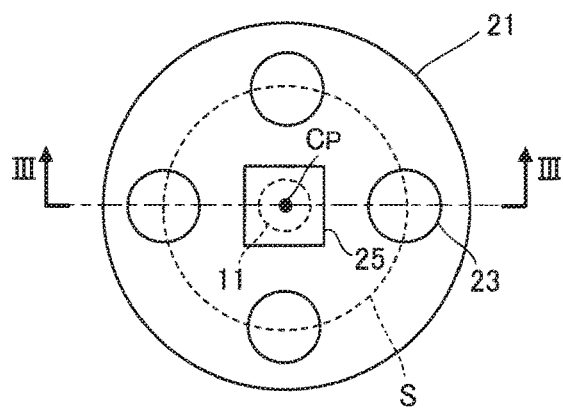
FIG. 2 is a plan view of a detection device.
Figure 3:
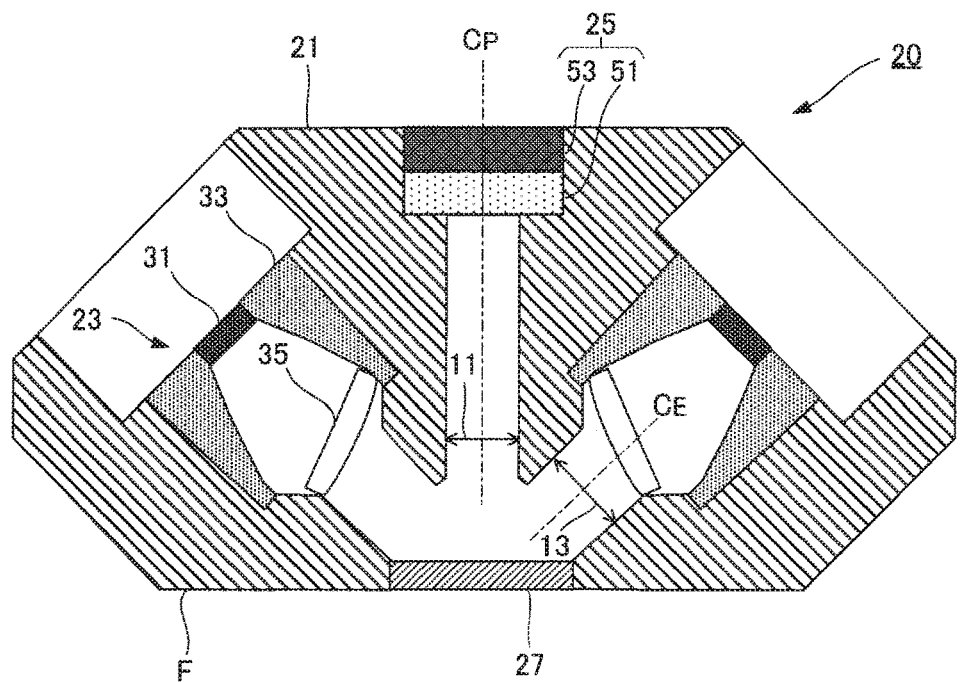
FIG. 3 is a sectional view taken along a III-III line in FIG. 2.

FIG. 2 is a plan view of the detection device FIG. 3 is a sectional view taken along a line in FIG. 2. As illustrated in FIGS. 2 and 3, the detection device 20 according to this embodiment includes a housing 21, a plurality of (four) light emitting sections 23, a light receiving section 25, and a protecting section 27. The housing 21 is a hollow structure and houses the light emitting sections 23, the light receiving section 25, and the protecting section 27. Specifically, the housing 21 includes a surface (hereinafter referred to as "opposed surface") F opposed to the surface of the measurement part M, a light receiving path 11, and an irradiation path 13. The opposed surface F is in contact with the surface of the measurement part M during measurement of a blood sugar level. The light receiving path 11 is a space circular in section formed from the opposed surface F toward the light receiving section 25. A center axis CP of the light receiving path 11 is perpendicular to the opposed surface F. The light receiving section 25 is located at an end portion on the opposite side of the opposed surface F in the light receiving path 11. The irradiation path 13 is a space circular in section in which lights emitted from the light emitting sections 23 pass. The irradiation path 13 is formed to branch from the light receiving path 11 and extend to the light emitting sections 23. A center axis OE of the irradiation path 13 is inclined with respect to the center axis CP of the light receiving path 11. The center axis CP of the light receiving path 11 coincides with the perpendicular of the opposed surface F. A light transmissive protecting section 27 (e.g., a glass plate) is set to cover the light receiving path 11. Note that, actually, it could be also assumed that the center axis CP of the light receiving path 11 and the perpendicular of the opposed surface F do not coincide with each other.

The light emitting sections 23 shown in FIG. 3 irradiate lights on the measurement part M (an organism). In this embodiment, the plurality of light emitting sections 23 simultaneously irradiate lights on the measurement part M. Each of the plurality of light emitting sections 23 includes a light source section 31, a reflector 33, and a lens 35. The light source section 31 emits light. A light emitting element such as an LED (Light Emitting Diode) or a halogen lamp can be used as the light source section 31. The light source section 31 in this embodiment emits light including near infrared light (approximately 800 nm to 1300 nm). As illustrated in FIG. 2, each of the four light emitting sections 23 is located on a circumference S around the center axis CP of the light receiving path 11.

The reflector 33 shown in FIG. 3 is a tubular structure. The light source section 31 is set at one end portion of the reflector 33. The lens 35 is located on the other end portion side. Light emitted from the light source section 31 is reflected on the inner surface of the reflector 33 to be guided to the lens 35.

The lens 35 allows the light emitted from the light source section 31 to pass. A convex lens that changes the light emitted from the light source section 31 to parallel light is suitably used as the lens 35. The light condensed by the lens 35 passes through the irradiation path 13 and the protecting section 27 to be irradiated on the surface of the measurement part M. The light made incident on the surface of the measurement part M is diffused and reflected on the inside (e.g., a blood vessel) of the measurement part M and then emitted to the detection device 20 side. The light emitted from the measurement part M passes through the protecting section 27 and the light receiving path 11 and reaches the light receiving section 25. That is, the light emitting sections 23 and the light receiving section 25 function as an optical sensor module of a reflection type.

The light receiving section 25 generates a detect ion signal corresponding to a light reception level of the lights irradiated from the light emitting sections 23 and passed through the organism (i.e., the measurement part M). The light receiving section 25 in this embodiment includes a spectroscope 51 and a light receiving element 53. The spectroscope 51 is set to be opposed to the measurement part M via the light receiving path 11 during measurement of a blood sugar level. The light receiving element 53 is set on the opposite side of the measurement part M across the spectroscope 51. Specifically, the spectroscope 51 is an optical device that spectrally disperses arriving light. For example, a Fabry-Perot interferometer (etalon) is suitably used as the spectroscope 51. Light in a near infrared region among lights made incident on the surface of the spectroscope 51 from the light receiving path 11 is spectrally disperse. The light receiving element 53 generates a detection signal corresponding to a light reception level of the light spectrally dispersed by the spectroscope 51. For example, a photoelectric conversion element such as a photodiode (PD) is suitably used as the light receiving element 53. For example, the light receiving element 53 is formed of InGaAs (indium gallium arsenide) showing high sensitivity in the near infrared region. Note that the detection device 20 includes, for example, a driving circuit that drives the light emitting sections 23 with supply of a driving current, and an output circuit (e.g., an amplifier circuit and an A/D converter) that amplifies and A/D-converts an output signal of the light receiving section 25. However, illustration of the circuits is omitted in FIG. 2.

The first specifying section 40 specifies a blood sugar level from the detection signal generated by the detection device 20. Specifically, the specifying section 40 generates a light absorption spectrum from the detection signal and specifies a blood sugar level (glucose concentration) from the light absorption spectrum. A publicly-known technique such as a multiple regression analysis method can be optionally used to specify a blood sugar level for which a light absorption spectrum is used. A PLS (Partial Least Squares) regression analysis method, an independent component analysis method, and the like are illustrated as the multiple regression analysis method. The display section (e.g., a liquid crystal display panel) 60 displays the blood sugar level specified by the specifying section 40.

Figure 4:
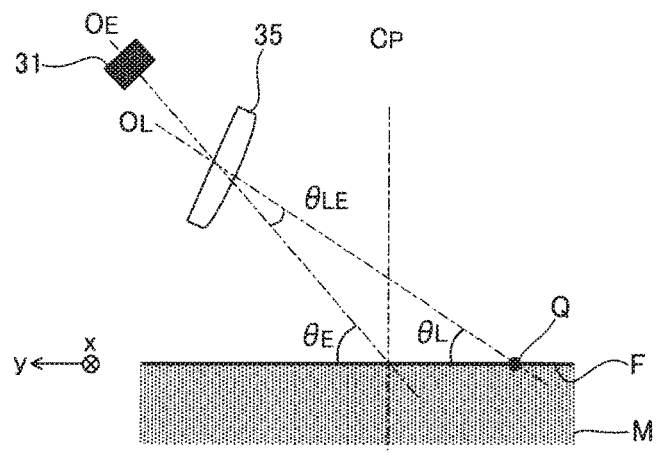
FIG. 4 is an explanatory diagram of a positional relation between a light source section and a lens.

FIG. 4 is an explanatory diagram of a positional relation between the light source section 31 and the lens 35. An optical axis OE of the light source section 31 and an optical axis OL of the lens 35 are respectively inclined at angles different from each other with respect to the opposed surface F. In other words, the optical axis OE of the light source section 31 and the optical axis OL of the lens 35 are inclined with respect to the center axis CP of the light receiving path 11 (the perpendicular of the opposed surface F). The optical axis OE of the light source section 31 is an imaginary axis representing a light beam emitted by the light source section 31. For example, an axis passing the center of the light emitting surface of the light source section 31 and perpendicular to the light emission surface is illustrated as the optical axis OE of the light source section 31. The optical axis OL of the lens 35 is an imaginary axis representing a light beam passing through the lens 35. For example, a straight line passing the center of a convex surface of the lens 35 and the center of gravity of the lens 35 is illustrated as the optical axis OL. In this embodiment, the optical axis OE of the light source section 31 crosses the center axis CP of the light receiving path 11. A surface passing an intersection of the optical axis OE and the center axis CP is the opposed surface F. In the following explanation, a direction of an intersection line of a plane including the optical axis OE of the light source section 31 and the optical axis OL of the lens 35 and the opposed surface F is represented as a "y direction" and a direction perpendicular to the y direction in the opposed surface F is represented as an "x direction". A point where the optical axis OL of the lens 35 and the surface of the measurement part M cross is represented as an intersection Q.

Specifically, the light source section 31 and the lens 35 are set such that an angle $\theta L$ formed by the opposed surface F and the optical axis OL of the lens 35 is smaller than an angle $\theta E$ formed by the opposed surface F and the optical axis OE of the light source section 31. That is, the inclination of the optical axis OE of the light source section 31 with respect to the opposed surface F is large compared with the optical axis OL of the lens 35. The angle $\theta L$ and the angle $\theta E$ are smaller than 90 degrees. The angle $\theta E$ is, for example, 45 degrees. The angle $\theta L$ is smaller than 45 degrees. The optical axis OE of the light source section 31 in this embodiment crosses the optical axis OL of the lens 35 on the inside of the lens 35. Note that a configuration can also be adopted in which the optical axis OE of the light source section 31 and the optical axis OL of the lens 35 cross on the outside of the lens 35. An angle $\theta LE$ formed by the optical axis OL of the lens 35 and the optical axis OE of the light source section increases as the angle $\theta L$ decreases. The angle $\theta LE$ approaches 0 degree as the angle $\theta L$ approaches the angle $\theta E$.

Figure 5:
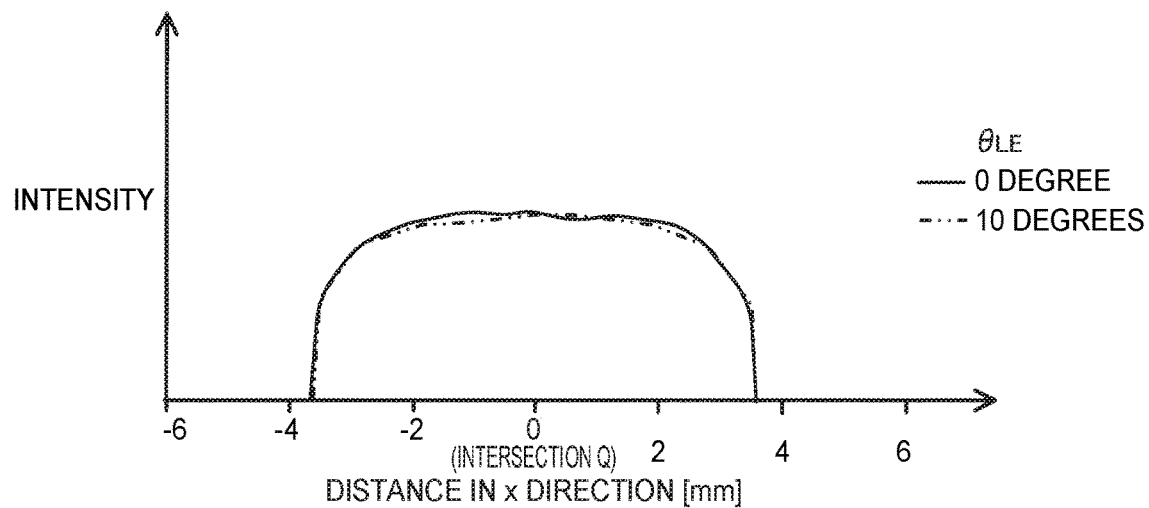
FIG. 5 is a graph showing an intensity distribution of light in an x direction in an irradiation range.
Figure 6:
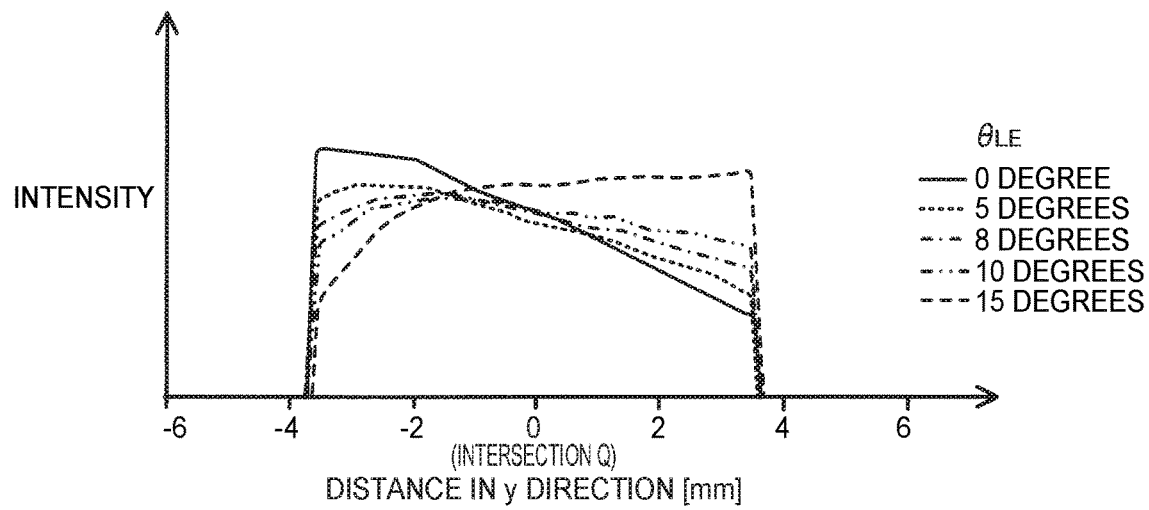
FIG. 6 is a graph showing an intensity distribution of light in a y direction in the irradiation range.
Figure 7:
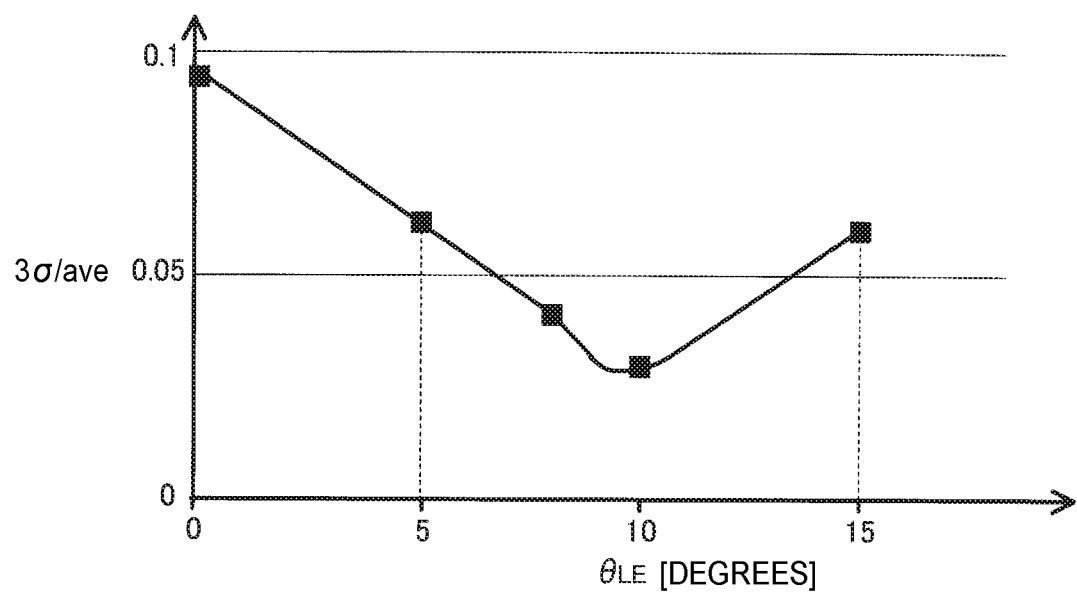
FIG. 7 is a graph showing a relation between a dispersion degree of the intensity of the light in the y direction and an angle formed by an optical axis of the lens and an optical axis of the light source section.

FIGS. 5 and 6 are graphs showing, concerning a plurality of cases in which the angle $\theta LE$ of the optical axis OE and the optical axis OL is changed, an intensity distribution of light in a range in which light emitted from the light emitting section 23 is irradiated on the surface of the measurement part M (hereinafter referred to as "irradiation range"). FIG. 5 shows the intensities of the light at respective distances from the intersection Q in the x direction (i.e., an intensity distribution in the x direction). FIG. 6 shows the intensities of the light at respective distances from the intersection Q in the y direction (i.e., an intensity distribution in the y direction). FIG. 7 is a graph showing a relation between a dispersion degree ($3\sigma$/ave) of the intensities of the light in the y direction and the angle $\theta LE$. The sign $\sigma$ means a standard deviation of the intensities. The sign ave means an average of the intensities. The dispersion degree ($3\sigma$/ave) is an indicator indicating a degree of dispersion of the intensities. There is a tendency that, as the dispersion degree ($3\sigma$/ave) is smaller, a difference of the intensities of the light in the irradiation range is smaller (the intensities of light are closer to uniform intensity).

As illustrated in FIG. 5, in the x direction, there is no difference in the intensity distribution when the angle $\theta LE$ is 0 degree and when the angle $\theta LE$ is 10 degrees. That is, the influence of the angle $\theta LE$ is small in the intensity distribution in the x direction. On the other hand, as illustrated in FIGS. 6 and 7, in they direction, when the angle $\theta LE$ is larger than 0 degree, a difference in the intensity of light (irradiation unevenness) within the irradiation range is reduced compared with when the angle $\theta LE$ is 0 degree (i.e., the optical axis OE and the optical axis OL coincide with each other). In particular, when the angle $\theta LE$ is 5 degrees or more and 15 degrees or less, the difference in the intensity of the light (the irradiation unevenness) within the irradiation range is further reduced compared with when the angle $\theta LE$ is 0 degree. In order to highly accurately specify a blood sugar level, it is desirable to irradiate uniform light on the measurement part M. Therefore, in this embodiment, the light source section 31 and the lens 35 are set such that the angle $\theta L$ formed by the opposed surface F and the optical axis OL of the lens 35 is smaller than the angle $\theta E$ formed by the opposed surface F and the optical axis OE of the light source section 31. More desirably, the light source section 31 and the lens 35 are set such that the angle $\theta LE$ is 5 degrees or more and 15 degrees or less. Note that the angle $\theta LE$ may be differentiated among the plurality of light emitting sections 23.

In this embodiment, since the optical axis OE of the light source section 31 is inclined with respect to the opposed surface F, there is an advantage that diffused reflected light is easily obtained from the inside of the measurement part M (the organism) compared with a configuration in which the optical axis OE of the light source section 31 is not inclined with respect to the opposed surface F (i.e., a configuration in which the optical axis OE and the perpendicular of the opposed surface F coincide with each other). In this embodiment, in particular, since the angle $\theta L$ formed by the oppose surface F and the optical axis OL of the lens 35 is smaller than the angle $\theta E$ formed by the opposed surface F and the optical axis OE of the light source section 31, it is possible to reduce the difference in the intensity of the light irradiated on the measurement part M (ideally, irradiate uniform light on the measurement part M). Further, it possible to highly accurately specify biological information.

Modifications

The form illustrated above can be variously modified. Specific forms of modifications are illustrated below. Two or more forms optionally selected out of the following illustration can be combined as appropriate.

(1) In the form explained above, the plurality of (four) light emitting sections 23 simultaneously emit lights on the organism. However, a part of the plurality of light emitting sections 23 (e.g., one light emitting section 23) may irradiate light. Even if any one of the plurality of light emitting elements 23 irradiates light on the measurement part M, the effect of reducing the difference in the intensity of the light irradiated on the measurement part M is realized. That is, in the invention, the detection device 20 does not always need to include the plurality of light emitting sections 23. However, with the form in which the detection device 20 includes the plurality of light emitting sections 23, it is possible to reduce noise due to the influence of a tissue (e.g., a sweat gland and body hair) other than the organism inside from, for example, a plurality of detection signals generated by sequentially causing the plurality of light emitting sections 23 to emit lights. Therefore, it is possible to highly accurately specify a blood sugar level. In the form in which the detection device 20 includes the plurality of light emitting sections 23, by changing the number of the light emitting sections 23 caused to emit lights among the plurality of light emitting sections 23, it is possible to change depth that light reaches in the measurement part M. Therefore, it is possible to generate a detection signal that has passed a specific region (e.g., an artery) in the organism. Further, it is possible to generate a detection signal optimum for specifying a blood sugar level. As it is understood from the above explanation, the number of the light emitting sections 23 included in the detection device 20 is optional.

(2) In the form explained above, the lens 35 and the light source section 31 are set such that the angle θLE formed by the optical axis OL of the lens 35 and the optical axis OE of the light source section 31 is 5 degrees or more and 15 degrees or less. However, the angle θLE is not limited to the above illustration. The angle θLE is optional if the action of the light emitted from the light source section 31 reaching the measurement part M via the lens 35 is obtained and the angle θL is in a range in which a condition that the angle θL is smaller than the angle θE is satisfied. However, with the configuration in which the angle θLE 5 degrees or more and 15 degrees or less, the effect of reducing the difference in the intensity of the light irradiated on the measurement part M irradiate uniform light on the measurement part M) is conspicuous.

(3) In the form explained above, the blood sugar level is specified as the biological information. However, a type of biological information to be specified is not limited to the above illustration. For example, various blood component concentrations such as hemoglobin concentration, blood oxygen concentration, and neutral fat concentration may be specified as the biological information.

(4) In the form explained above, the near infrared light is included in the light emitted by the light emitting section 23. However, a wavelength region of the light emitted by the light emitting section 23 is optional. However, the configuration in which the near infrared light is included in the light emitted by the light emitting section 23 is particularly effective when the blood sugar level is specified as the biological information. That is, the wavelength region of the light emitted by the light emitting section 23 can be optionally changed according to the type of the biological information to be specified.

(5) In the form explained above, the light receiving section 25 includes the spectroscope 51 and the light receiving element 53. However, the configuration of the light receiving section 25 is optional if the light receiving section 25 can generate a detection signal corresponding to a light reception level of light emitted from the light emitting section 23 and passed through the inside of the measurement part M. For example, a configuration in which the light receiving section includes only the light receiving element 53 or configuration in which the light receiving section 25 includes a band-pass filter between the spectroscope 51 and the light receiving element 53 when a Fabry-Perot interferometer is used as the spectroscope 51 can also be adopted.

(6) In the form explained above, the biological information measuring device 1 includes the display section 60. However, the display section 60 can also be provided in a terminal device capable of communicating with the biological information measuring device 1 (by wire or radio). The biological information measuring device 1 transmits a specified blood sugar level to the terminal device. The terminal device displays the blood sugar level. That is, the display section 60 is not essential in the biological information measuring device 1.

(7) A configuration may be adopted in which one or both of the specifying section 40 and the display section 60 are provided in the terminal device (e.g., realized by an application executed in the terminal device). That is, the biological information measuring device 1 is also realized by a plurality of devices configured separately from one another.

The entire disclosure of Japanese Patent Application No. 2017-132518, filed Jul. 6, 2017 is expressly incorporated by reference herein.

What is claimed is:

1. A detection device comprising:
a first light source which emits first light;
a first lens;
a second light source which emits second light;
a second lens;
a light transmissive protecting plate, a length between the first light sources and the light transmissive protecting plate being larger than a length between the first lens and the light transmissive protecting plate, a length between the second light sources and the light transmissive protecting plate being larger than a length between the second lens and the light transmissive protecting plate; and
a light receiver which receives the first light and the second light,
wherein the first light source and the second light source are located on a circumference around a center axis of the light receiver,
an angle formed by an optical axis of the first lens and the light transmissive protecting plate is smaller than an angle formed by an optical axis of the first light source and the transmissive protecting plate, and
an angle formed by an optical axis of the second lens and the light transmissive protecting plate is smaller than an angle formed by an optical axis of the second light source and the transmissive protecting plate.

2. The detection device according to claim 1, wherein
an angle formed by the optical axis of the first lens and the optical axis of the first light source is 5 degrees or more and 15 degrees or less, and
an angle formed by the optical axis of the second lens and the optical axis of the second light source is 5 degrees or more and 15 degrees or less.

3. A biological information measuring device comprising:
the detection device according to claim 1; and
a specifying section configured to specify biological information from a detection signal generated by the detection device.

4. A biological information measuring device comprising:
the detection device according to claim 2; and
a specifying section configured to specify biological information from a detection signal generated by the detection device.

* * * * *